United States Patent [19]

Bright

[11] Patent Number: 5,616,770
[45] Date of Patent: Apr. 1, 1997

[54] 1,4-CYCLOHEXANEDIMETHANOL BIS (DIARYL PHOSPHATE)

[75] Inventor: Danielle A. Bright, New City, N.Y.

[73] Assignee: Akzo Nobel, NV, Arnhem, Netherlands

[21] Appl. No.: 608,266

[22] Filed: Feb. 28, 1996

[51] Int. Cl.$^6$ ........................................... C07F 9/12
[52] U.S. Cl. ............................... 558/161; 524/127
[58] Field of Search ................................ 558/161

[56] References Cited

U.S. PATENT DOCUMENTS

| | | | |
|---|---|---|---|
| 3,869,526 | 3/1975 | Combey et al. | 260/929 |
| 4,343,732 | 8/1982 | Zama et al. | 524/114 |

FOREIGN PATENT DOCUMENTS 1532904  11/1978  United Kingdom ............. C07F 9/08

*Primary Examiner*—Johann Richter
*Assistant Examiner*—Michael G. Ambrose
*Attorney, Agent, or Firm*—Richard P. Fennelly; Louis A. Morris

[57] ABSTRACT

Novel flame retardant compounds for polymers are disclosed that include 1,4-cyclohexanedimethanol bis(diphenyl phosphate)s. These can be synthesized by reacting 1,4-cyclohexanedimethanol and a diphenyl halophosphate, such as diphenyl chlorophosphate, in the presence of a catalyst, such as magnesium chloride, in an appropriate solvent, such as hexane.

6 Claims, No Drawings

1,4-CYCLOHEXANEDIMETHANOL BIS (DIARYL PHOSPHATE)

BACKGROUND OF THE INVENTION

The prior art discloses a wide variety of diphosphate flame retardant compounds which contain two phosphate groups (often containing two phenyl substituents each) linked together by a bridging group —O—R—O—, where R comprises an arylene or alkylene group. Certain disclosures exist which include cyclohexylene as a possible alkylene group for R, including U.S. Pat. No. 3,869,526 to M. Combey et al. (see Col. 1, line 27) and U.S. Pat. No. 4,343,732 to T. Zama et al. (see Col. 3, lines 52–53).

SUMMARY OF THE INVENTION

The present invention relates to 1,4-cyclohexanedimethanol bis(diaryl phosphate)s, which are useful as flame retardant compounds for polymers. This class of compound can be synthesized by reacting 1,4-cyclohexanedimethanol and a diaryl halophosphate, such as diphenyl chlorophosphate, in the presence of a catalyst, such as magnesium chloride, either with or without an appropriate solvent, such as hexane.

DESCRIPTION OF PREFERRED EMBODIMENTS

The term "1,4-cyclohexanedimethanol bis(diaryl phosphate)s" as used herein is intended to cover a novel class of diphosphate flame retardant compounds of the general formula

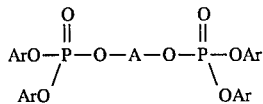

where Ar is either unsubstituted or substituted (e.g., lower alkyl substituted, halo, or alkoxy) aryl group (e.g., phenyl), A is a hydrocarbylene-containing bridging group of the formula $CH_2$—$C_6H_4$—$CH_2$ and is derived from 1,4-cyclohexanedimethanol. A preferred compound is one containing unsubstituted phenyl as Ar, namely, 1,4-cyclohexanedimethanol bis(diphenyl phosphate).

The subject compounds can be easily formed by the reaction of 1,4-cyclohexanedimethanol and the desired diphenyl halophosphate in the presence of a catalyst in an appropriate solvent at elevated temperatures of from about 90° C. to about 150° C., preferably, in a ratio of one mole of cyclohexanedimethanol to two moles of diaryl phosphate.

The diphenyl moiety on the selected diphenyl halophosphate reagent can be either unsubstituted or can be substituted, e.g., with one or more lower alkyl groups, halo groups, or alkoxy groups depending upon the type of product desired. The halo- moiety in this reagent can be either chloro or bromo with the former being preferred.

The solvent medium which is used can be, for example, an aliphatic solvent, such as heptane, or an aromatic solvent, such as toluene.

The catalyst that is used can be a Lewis acid catalyst such as magnesium chloride, aluminum chloride, titanium tetrachloride, zinc dichloride, and the like, in an amount of from about 0.05% to about 0.5%, by weight of the reactants, in a particularly preferred embodiment.

The following Examples further illustrate this invention and its characteristics.

EXAMPLE 1

This Example illustrates the synthesis of 1,4-cyclohexanedimethanol bis(diphenyl phosphate).

The following reagents and solvent were heated to reflux: 1,4-cyclohexanedimethanol (0.25 mole, 36.0 gm); diphenyl chlorophosphate (0.5 mole, 134.3 gm); magnesium chloride (250 mg); and hexane (34 gm, 52 ml). The progress of the reaction was monitored by infrared spectroscopy. After about four and one half hours, the reaction was completed, and 150 ml of methanol was added to the reaction medium. The desired product crystallized from the reaction medium. After filtration, washing and drying, there was left 124.9 gm of a white solid (82.2% yield, over 90% purity by liquid chromatography) having a melting point of 70°–75° C. The structure of the 1,4-cyclohexanedimethanol bis(diphenyl phosphate) product was confirmed by proton and $^{31}P$ nmr.

EXAMPLE 2

In this Example, 94.4 parts by weight of high impact strength polystyrene (HIPS) and 5.6 parts by weight of the 1,4-cyclohexanedimethanol bis(diphenyl phosphate) product from Example 1 were compounded and extruded. The Limiting Oxygen Index (LOI) of the piece was 20.5 as compared to 18 for a HIPS sample not containing the flame retardant additive.

The foregoing Example should not be construed in a limiting sense since it is intended to merely recite certain embodiments of the claimed invention. The scope of protection sought is set forth in the claims which follow.

I claim:

1. 1,4-cyclohexanedimethanol bis (diaryl phosphate) wherein aryl may be substituted.

2. 1,4-cyclohexanedimethanol bis(diphenyl phosphate) wherein phenyl may be substituted.

3. Compounds as claimed in claim 1 wherein the diaryl moieties are unsubstituted.

4. Compounds as claimed in claim 1 wherein the diaryl moieties are substituted with at least one substituent selected from the group consisting of lower alkyl, halo, and alkoxy.

5. A compound as claimed in claim 2 wherein the diphenyl moieties are unsubstituted.

6. A compound as claimed in claim 2 wherein the diphenyl moieties are substituted with at least one lower alkyl group.

* * * * *